(12) United States Patent
Ota et al.

(10) Patent No.: US 12,050,186 B2
(45) Date of Patent: *Jul. 30, 2024

(54) STEEL DECK BRIDGE EVALUATION DEVICE, STEEL DECK BRIDGE EVALUATION METHOD, AND PROGRAM

(71) Applicant: GEO SEARCH CO., LTD., Tokyo (JP)

(72) Inventors: Masahiko Ota, Tokyo (JP); Hideaki Morita, Tokyo (JP); Akiko Shiozawa, Tokyo (JP)

(73) Assignee: GEO SEARCH CO., LTD., Tokyo (JP)

( * ) Notice: Subject to any disclaimer, the term of this patent is extended or adjusted under 35 U.S.C. 154(b) by 385 days.

This patent is subject to a terminal disclaimer.

(21) Appl. No.: 17/600,225

(22) PCT Filed: Mar. 17, 2020

(86) PCT No.: PCT/JP2020/011752
§ 371 (c)(1),
(2) Date: Sep. 30, 2021

(87) PCT Pub. No.: WO2020/203262
PCT Pub. Date: Oct. 8, 2020

(65) Prior Publication Data
US 2022/0205929 A1    Jun. 30, 2022

(30) Foreign Application Priority Data
Apr. 1, 2019   (JP) ................................ 2019-069817

(51) Int. Cl.
*G01N 22/02*    (2006.01)
*G01N 33/2045*  (2019.01)

(52) U.S. Cl.
CPC ......... *G01N 22/02* (2013.01); *G01N 33/2045* (2019.01)

(58) Field of Classification Search
CPC . G01N 22/02; G01N 33/2045; G01M 5/0091; G01M 5/0008
See application file for complete search history.

(56) References Cited

U.S. PATENT DOCUMENTS 5,206,640 A * 4/1993 Hirvonen ................. G01V 3/02
                                                      324/72
6,772,091 B1    8/2004 Roberts
(Continued)

FOREIGN PATENT DOCUMENTS

CN    114580493 A  *  6/2022
JP    S6117051 A   *  1/1986
(Continued)

OTHER PUBLICATIONS

Hideaki et al., "Development and application of bridge deck deterioration diagnosis system utilizing skeleka technology", Lecture Summaries of the 66th Annual Academic Lecture Conference of Japan Society of Civil Engineers, 156:1-2 (2011).
(Continued)

*Primary Examiner* — Octavia Hollington
(74) *Attorney, Agent, or Firm* — MARSHALL, GERSTEIN & BORUN LLP

(57) ABSTRACT

A steel deck bridge evaluation device includes a processor configured to acquire reflected response data relating to a reflected response to an electromagnetic wave irradiated through a surface of a deck in a depth direction of the deck, remove a first frequency component obtained by reflection of the electromagnetic wave at a surface of the deck and a second frequency component obtained by reflection of the electromagnetic wave at a steel deck from a reflected response frequency distribution of the reflected response expressing the reflected response data, and evaluate damage to or deterioration of the deck using a peak measurement value that is a peak value of a frequency component level
(Continued)

corresponding to a specific frequency or higher, in the reflected response frequency distribution from which the first frequency component and the second frequency component have been removed.

10 Claims, 11 Drawing Sheets

(56) References Cited

U.S. PATENT DOCUMENTS

| | | | | |
|---|---|---|---|---|
| 8,596,136 B2* | 12/2013 | Hecht | .................... | E02D 33/00 73/803 |
| 9,377,528 B2* | 6/2016 | Birken | .................. | G01S 13/885 |
| 9,970,905 B2* | 5/2018 | Volker | .................. | G01N 29/043 |
| 2013/0018575 A1 | 1/2013 | Birken et al. | | |
| 2022/0230290 A1* | 7/2022 | Morita | .................... | G06T 7/001 |
| 2022/0412875 A1* | 12/2022 | Morita | .................. | G01N 22/00 |

FOREIGN PATENT DOCUMENTS

| | | | | |
|---|---|---|---|---|
| JP | 8-62338 A | | 3/1996 | |
| JP | H0862338 A | * | 3/1996 | |
| JP | H10253595 A | * | 9/1998 | |
| JP | 2000028583 A | * | 1/2000 | |
| JP | 2011-112403 A | | 6/2011 | |
| JP | 5740509 B1 | * | 6/2015 | |
| JP | 2015-197434 A | | 11/2015 | |
| JP | 2015-215332 A | | 12/2015 | |
| JP | 2016188545 A | * | 11/2016 | |
| JP | 2016191697 A | * | 11/2016 | |
| JP | 64-51939 B2 | | 1/2019 | |
| JP | 6675656 B1 | * | 4/2020 | ............ G01N 22/02 |
| KR | 100784072 B1 | * | 12/2007 | |
| WO | WO-2018/105106 A1 | | 6/2018 | |

OTHER PUBLICATIONS

International Search Report and Written Opinion for Application No. PCT/JP2020/011752, dated Jun. 23, 2020.

* cited by examiner

STEEL DECK BRIDGE EVALUATION DEVICE, STEEL DECK BRIDGE EVALUATION METHOD, AND PROGRAM

TECHNICAL FIELD

This application claims priority from Japanese Patent Application No. 2019-069817 filed on Apr. 1, 2019, the disclosure of which is incorporated in its entirety by reference herein.

Technology disclosed herein relates to a steel deck bridge evaluation device, a steel deck bridge evaluation method, and a non-transitory storage medium.

BACKGROUND ART

Hitherto, image diagnostics employing electromagnetic waves have been employed to evaluate internal damage to or deterioration of steel deck bridges (road surface structures) employed as elevated roads, road bridges, or the like.

For example, a method has been proposed for surveying damage to a steel deck pavement by irradiating an electromagnetic wave from above a survey object surface to below the survey object surface, and detecting multiple reflected wave data for this electromagnetic wave. Even after a detection timing of a first wave reflected at a steel deck has passed, a reflected wave detected after a duration corresponding to a total travel path length of the reflected wave has elapsed is regarded as a wave reflected at a plane at a virtual survey depth, or a through-pavement wave that has passed along the travel path. Noise is removed from the observed waves by performing background subtraction processing for each virtual depth, enabling damaged portions to be observed in isolation. In addition, a maximum value of reflected wave intensity of the reflected waves detected for each of plural different virtual depths is set as an overlay processing value, and damaged pavement locations are displayed so as to be expressed according to damage levels in an overlaid horizontal surface image created from the reflected wave intensities after the overlay processing (see, for example, Japanese Patent Application Laid-Open (JP-A) No. 2015-215332).

SUMMARY OF INVENTION

Technical Problem

However, the image diagnostics of the above-described method are not capable of diagnosing which out of surface layer asphalt, mastic asphalt, or a steel deck configuring the steel deck bridge is suffering from damage to or deterioration. With steel deck bridges, the ability to distinguish between damage to or deterioration of the surface layer asphalt and damage to or deterioration of the mastic asphalt and steel deck would be particularly desirable.

Damage to or deterioration of the surface layer asphalt can be simply resolved by removing and repairing the asphalt, and so there is minimal effect on the steel deck structure. On the other hand, damage to or deterioration of the mastic asphalt leads to a drop in water resistance, a cause of corrosion of the steel deck which promotes damage or deterioration of the steel deck. Repairing damage to or deterioration of a steel deck is an extensive task. The ability to identify and distinguish damage to or deterioration of the mastic asphalt and steel deck from damage to or deterioration of the surface layer asphalt is therefore desirable.

However, the image diagnostics employed in conventional technology require a professional engineer to look at an image in order to determine sound portions and deteriorated portions of a steel deck bridge in relative terms. Qualitative evaluation such as this is difficult to interpret without specialist technical knowledge.

In consideration of the above circumstances, the present disclosure provides a steel deck bridge evaluation device, a steel deck bridge evaluation method, and a non-transitory storage medium that enable quantitative evaluation of damage to or deterioration of mastic asphalt and a steel deck within a steel deck bridge.

Solution to Problem

A steel deck bridge evaluation device according to a first aspect evaluates damage to or deterioration of a steel deck bridge in which a steel deck is embedded under asphalt. The evaluation device includes an acquisition section configured to acquire reflected response data relating to a reflected response to an electromagnetic wave irradiated through a surface of the steel deck bridge in a depth direction of the steel deck bridge, a removal section configured to remove a first frequency component obtained by reflection of the electromagnetic wave at the surface of the steel deck bridge and a second frequency component obtained by reflection of the electromagnetic wave at the steel deck from a reflected response frequency distribution of the reflected response expressing the reflected response data acquired by the acquisition section, and an evaluation section configured to evaluate damage to or deterioration of the steel deck bridge using a peak measurement value that is a peak value of a frequency component level corresponding to a specific frequency or higher, in the reflected response frequency distribution from which the first frequency component and the second frequency component have been removed by the removal section.

In a steel deck bridge evaluation device according to a second aspect, the evaluation section is configured to take, as a reference value, a peak value of a frequency component level corresponding to the specific frequency or higher, in a reference frequency distribution that is a reflected response frequency distribution obtained by removing the first frequency component and the second frequency component from a reflected response acquired by irradiating an electromagnetic wave into a steel deck bridge that has not deteriorated, and evaluate a degree of damage to or deterioration of the steel deck bridge by comparing the peak measurement value with the reference value.

In a steel deck bridge evaluation device according to a third aspect, the evaluation section is configured to perform evaluation by taking, as a proportional deterioration, a proportion of a difference between the reference value and the peak measurement value relative to the reference value.

In a steel deck bridge evaluation device according to a fourth aspect, the evaluation section is configured to set a predetermined proportion relative to the reference value as a threshold, and evaluate the steel deck bridge as having deteriorated in a case in which the peak measurement value is lower than the threshold.

In a steel deck bridge evaluation device according to a fifth aspect, the evaluation section is configured to evaluate damage to or deterioration of the steel deck bridge at plural positions on the surface of the steel deck bridge.

A steel deck bridge evaluation method according to a sixth aspect is a steel deck bridge evaluation method to evaluate damage to or deterioration of a steel deck bridge in which a steel deck is embedded under asphalt. The evaluation method includes an acquisition step of acquiring reflected response data relating to a reflected response to an electromagnetic wave irradiated through a surface of the steel deck bridge in a depth direction of the steel deck bridge, a removal step of removing a first frequency component obtained by reflection of the electromagnetic wave at the surface of the steel deck bridge and a second frequency component obtained by reflection of the electromagnetic wave at the steel deck from a reflected response frequency distribution of the reflected response expressing the reflected response data acquired in the acquisition step, and an evaluation step of evaluating damage to or deterioration of the steel deck bridge using a peak measurement value that is a peak value of a frequency component level corresponding to a specific frequency or higher, in the reflected response frequency distribution from which the first frequency component and the second frequency component have been removed in the removal step.

A program according to a seventh aspect is a program for evaluating damage to or deterioration of a steel deck bridge in which a steel deck is embedded under asphalt. The program causes a computer to execute processing including an acquisition step of acquiring reflected response data relating to a reflected response to an electromagnetic wave irradiated through a surface of the steel deck bridge in a depth direction of the steel deck bridge, a removal step of removing a first frequency component obtained by reflection of the electromagnetic wave at the surface of the steel deck bridge, and a second frequency component obtained by reflection of the electromagnetic wave at the steel deck from a reflected response frequency distribution of the reflected response expressing the reflected response data acquired in the acquisition step, and an evaluation step of evaluating damage to or deterioration of the steel deck bridge using a peak measurement value that is a peak value of a frequency component level corresponding to a specific frequency or higher, in the reflected response frequency distribution from which the first frequency component and the second frequency component have been removed in the removal step.

Advantageous Effects of Invention

The first aspect, the sixth aspect, and the seventh aspect enable quantitative evaluation of damage to or deterioration of mastic asphalt and a steel deck within a steel deck bridge.

DESCRIPTION OF EMBODIMENTS

Figure 1:
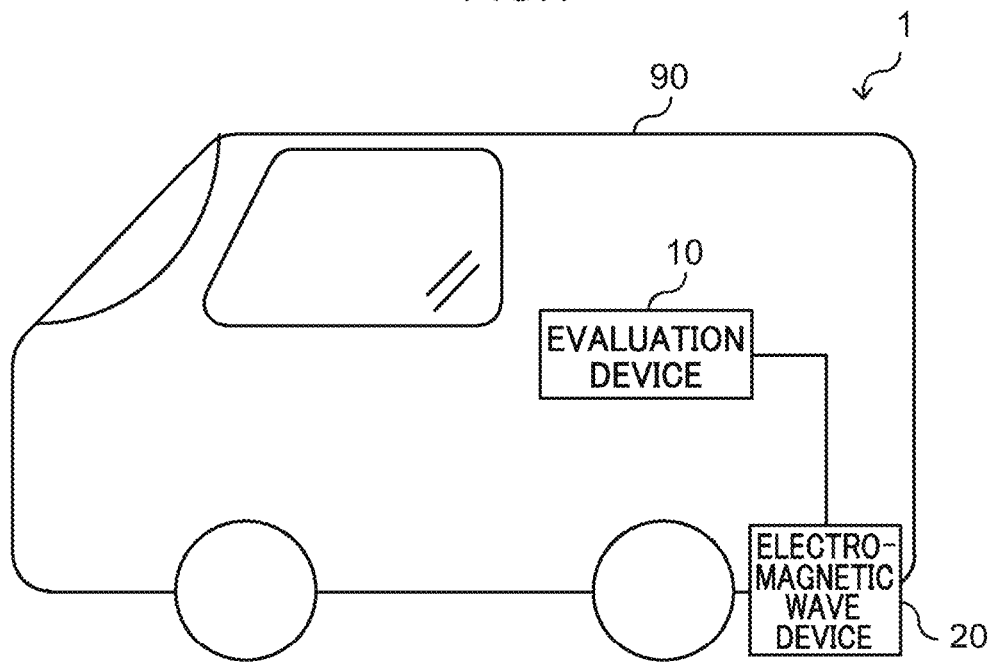
FIG. 1 is a schematic configuration diagram illustrating a deck evaluation system.

Explanation follows regarding an example of an exemplary embodiment of technology disclosed herein, with reference to the drawings. Note that the same or equivalent configuration elements and portions are allocated the same reference numerals in each of the drawings. Moreover, the dimensional proportions in the drawings may be exaggerated to aid explanation, and may therefore differ from actual proportions.

Evaluation is performed with regard to the degree of damage to or deterioration of mastic asphalt and the steel deck of a steel deck bridge, this being a road surface structure of a road bridge or the like.

Figure 2:
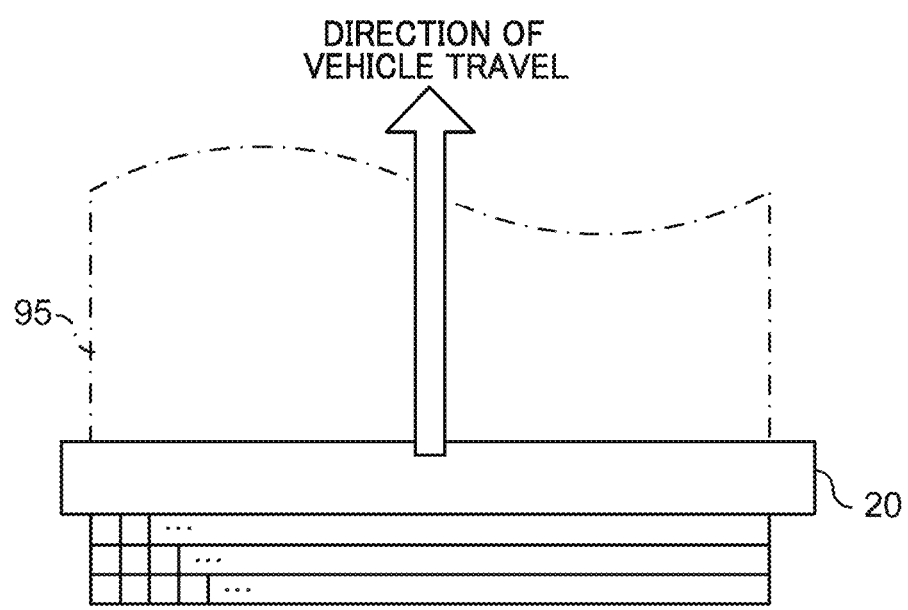
FIG. 2 is a diagram to explain detection of a reflected response waveform.
Figure 3:
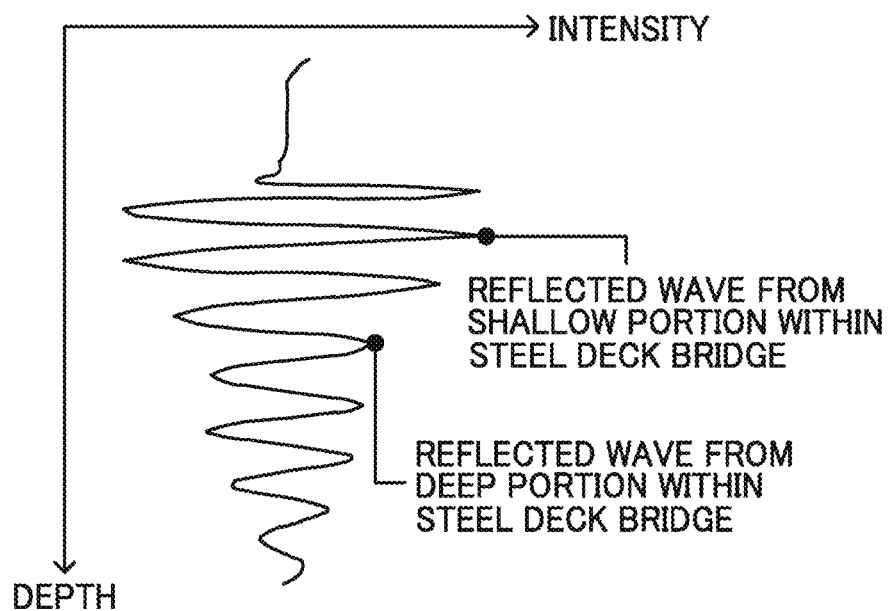
FIG. 3 is a diagram illustrating an example of a reflected response waveform detected for a single grid square.
Figure 4:
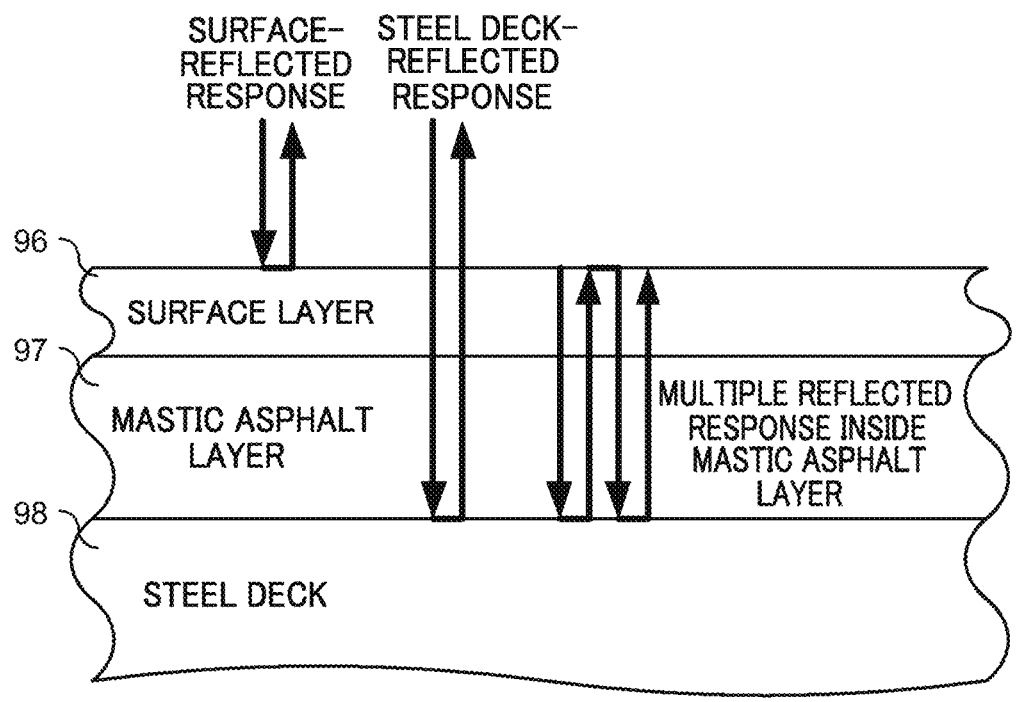
FIG. 4 is a cross-section schematically illustrating a steel deck bridge.

FIG. 1 is a diagram illustrating a schematic configuration of an evaluation system. FIG. 2 is a diagram to explain detection of a reflected response waveform. FIG. 3 is a diagram illustrating an example of a reflected response waveform detected for a single grid square. FIG. 4 is a schematic cross-section of a steel deck bridge.

As illustrated in FIG. 1, a steel deck bridge evaluation system 1 according to the present exemplary embodiment is installed in a vehicle 90.

The steel deck bridge evaluation system 1 is configured including a steel deck bridge evaluation device 10 and an electromagnetic wave device 20. The steel deck bridge evaluation device 10 is a device for evaluating a steel deck bridge in which a steel deck is embedded underneath asphalt. The steel deck bridge evaluation device 10 will be described in detail later. In the following explanation, the steel deck bridge evaluation system 1 is simply referred to as the evaluation system 1, and the steel deck bridge evaluation device 10 is simply referred to as the evaluation device 10. This similarly applies in the drawings.

The electromagnetic wave device 20 includes plural linearly arrayed electromagnetic wave irradiation elements and receiver elements. The electromagnetic wave device 20 is, for example, provided at a rear lower section of the vehicle 90 such that a direction of travel of the vehicle 90 corresponds to a bridge axis direction, and the linear array direction of the electromagnetic wave device 20 is a direction at right angles to the bridge axis. The electromagnetic wave irradiation elements irradiate electromagnetic waves such as microwaves toward the steel deck bridge. The receiver elements receive reflected waves reflected by respective locations of the steel deck bridge.

As illustrated in FIG. 2, the electromagnetic wave device 20 irradiates electromagnetic waves in a direction through the surface and into the interior of the steel deck bridge (a depth direction) and receives reflected waves while scanning an evaluation target range 95 on the road bridge surface in the direction of vehicle travel. Reflected wave intensities according to depth are thus detected for respective grid squares of the evaluation target range 95. The reflected wave intensities according to depth are detected in the form of a reflected response waveform for each of the grid squares, as illustrated in FIG. 3. As an example, each grid square measures 1 cm×1 cm, and the width of the one linear array is 2.0 m. In such a configuration, reflected response waveforms are detected for 200 grid squares on a single linear array.

The amount of time between irradiation of an electromagnetic wave and the reflected wave being received corresponds to the depth. As illustrated in FIG. 3, from the reflected response waveform, a reflected wave intensity can be obtained for each depth of the steel deck bridge by extracting a reflected wave intensity corresponding to each desired depth.

The electromagnetic wave device 20 outputs to the evaluation device 10 reflected response waveform information (reflected wave intensities according to depth) acquired for each grid square.

As illustrated in FIG. 4, a steel deck bridge is formed with layers including a steel deck pavement having a surface layer 96 and a mastic asphalt layer 97, and a steel deck 98. The surface layer 96 contains a fine-grained asphalt (dense graded asphalt). The steel deck 98 is embedded underneath the mastic asphalt layer 97. The electromagnetic waves irradiated from the electromagnetic wave device 20 are reflected by the surface layer 96 and the steel deck 98 at different timings. Electromagnetic waves are also received after being reflected repeatedly within the mastic asphalt layer 97. Thus, the reflected response from the steel deck bridge includes a surface-reflected response corresponding to reflection from the surface layer 96, a steel deck-reflected response corresponding to reflection from the steel deck 98, and a mastic asphalt layer multiple internal reflected response corresponding to repeated reflection within the mastic asphalt layer 97. These reflected responses are expressed by the reflected response waveform illustrated in FIG. 3. Note that the present exemplary embodiment describes a steel deck bridge containing mastic asphalt as an example. However, the steel deck bridge may contain a type of asphalt other than mastic asphalt. Moreover, the steel deck bridge does not necessarily have to be a bridge per-se, and may be any structural body with a road surface structure including the above-described structure.

Note that the electromagnetic wave device 20 is not limited to a configuration attached to the vehicle 90, and the electromagnetic wave device 20 may be held by a worker, built into a handcart, or the like.

Figure 5:
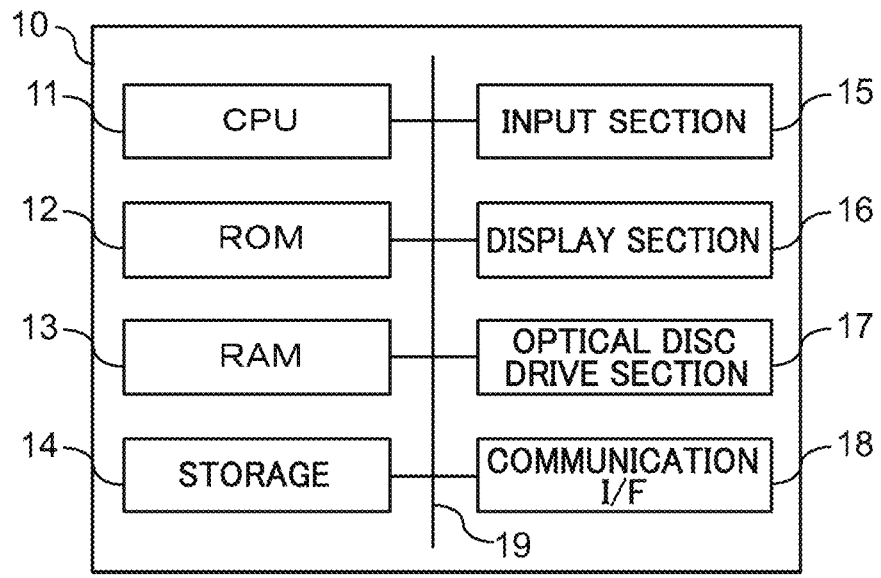
FIG. 5 is a block diagram illustrating a hardware configuration of an evaluation device.

FIG. 5 is a block diagram illustrating a hardware configuration of the evaluation device.

As illustrated in FIG. 5, the evaluation device 10 includes a central processing unit (CPU) 11, read only memory (ROM) 12, random access memory (RAM) 13, storage 14, an input section 15, a display section 16, an optical disc drive section 17, and a communication interface (communication I/F) 18. The respective configurations are connected so as to be capable of communicating with each other through a bus 19.

The CPU 11 is a central processing unit that executes various programs and controls various sections. Namely, the CPU 11 reads a program from the ROM 12 or the storage 14, and executes the program using the RAM 13 as a workspace. The CPU 11 controls respective configurations and performs various arithmetic processing according to the program recorded in the ROM 12 or the storage 14. In the present exemplary embodiment, an evaluation program (steel deck bridge evaluation program) for evaluating steel deck bridges is held in the ROM 12 or the storage 14.

The ROM 12 holds various programs and various data. The RAM 13 acts as a workspace to temporarily store programs or data. The storage 14 is configured by a hard disk drive (HDD) or a solid state drive (SSD), and holds various programs including an operating system, as well as various data.

The input section 15 includes a keyboard and a pointing device such as a mouse, and is used to perform various input. The display section 16 is for example a liquid crystal display used to display various information. The display section 16 may take the form of a touch panel and thereby also function as the input section 15.

The optical disc drive section 17 reads data stored on various recording media such as compact disc read only memory (CD-ROM) or Blu-ray discs, and also writes data to such recording media.

The communication interface 18 is an interface employing a protocol such as Ethernet (registered trademark), FDDI, or Wi-Fi (registered trademark) to communicate with other equipment.

Next, explanation follows regarding functional configuration of the evaluation device 10.

Figure 6:
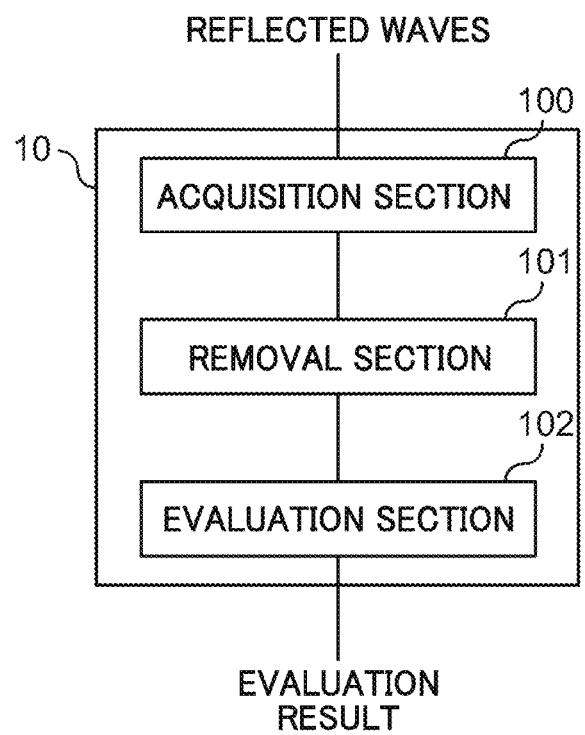
FIG. 6 is a block diagram illustrating an example of a functional configuration of an evaluation device.

FIG. 6 is a block diagram illustrating an example of functional configuration of the evaluation device.

As illustrated in FIG. 6, the evaluation device 10 includes an acquisition section 100, a removal section 101, and an evaluation section 102 as functional configurations. Each of these functional configurations is implemented by the CPU 11 reading the evaluation program stored in the ROM 12 or the storage 14, and expanding and executing the evaluation program in the RAM 13.

The acquisition section 100 acquires reflected response data relating to the reflected response to the electromagnetic waves irradiated through the surface of the steel deck bridge in the depth direction of the steel deck bridge. The acquisition section 100 acquires this reflected response data from the electromagnetic wave device 20.

From out of a frequency distribution of the reflected response expressing the reflected response data acquired by the acquisition section 100, the removal section 101 removes a first frequency component obtained as a result of electromagnetic wave reflection at the surface of the steel deck bridge, and a second frequency component obtained as a result of electromagnetic wave reflection at the steel deck. The first frequency component is a reflection frequency component obtained for the vicinity of the surface of the steel deck pavement (a range including the surface layer 96 and a boundary between the surface layer 96 and the mastic asphalt layer 97), and expresses the surface-reflected response illustrated in FIG. 4. The second frequency component is a reflection frequency component obtained for the vicinity of the surface of the steel deck 98 (a range including the mastic asphalt layer 97 and a boundary between the mastic asphalt layer 97 and the steel deck 98), and expresses the steel deck-reflected response illustrated in FIG. 4.

The evaluation section 102 evaluates the degree of damage to or deterioration of the steel deck bridge using a peak measurement value, this being a peak value of a frequency component level corresponding to a specific frequency or higher in the reflected response frequency distribution from which the first frequency component and the second frequency component have been removed by the removal section 101. The result of this evaluation by the evaluation section 102 is for example displayed on the display section 16.

Next, explanation follows regarding removal of the first frequency component and the second frequency component by the removal section 101.

Figure 7:
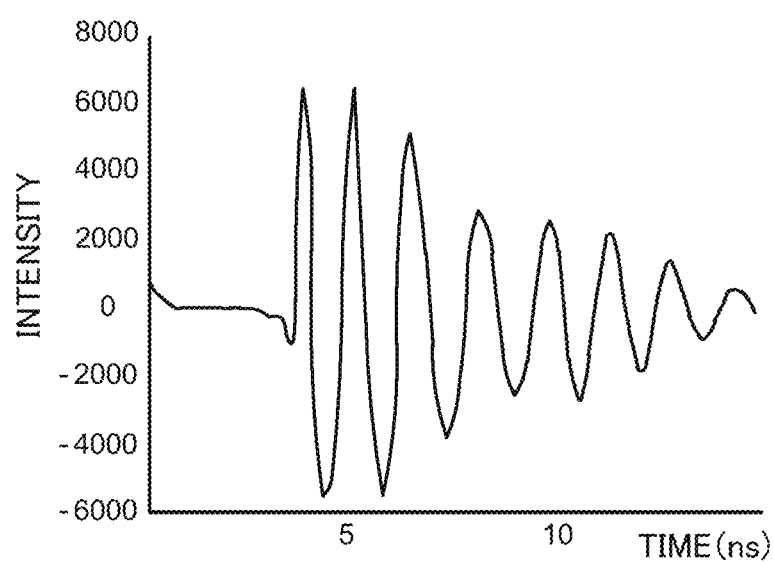
FIG. 7 is a diagram illustrating a reflected response based on reflected response data acquired from an electromagnetic wave device.
Figure 8:
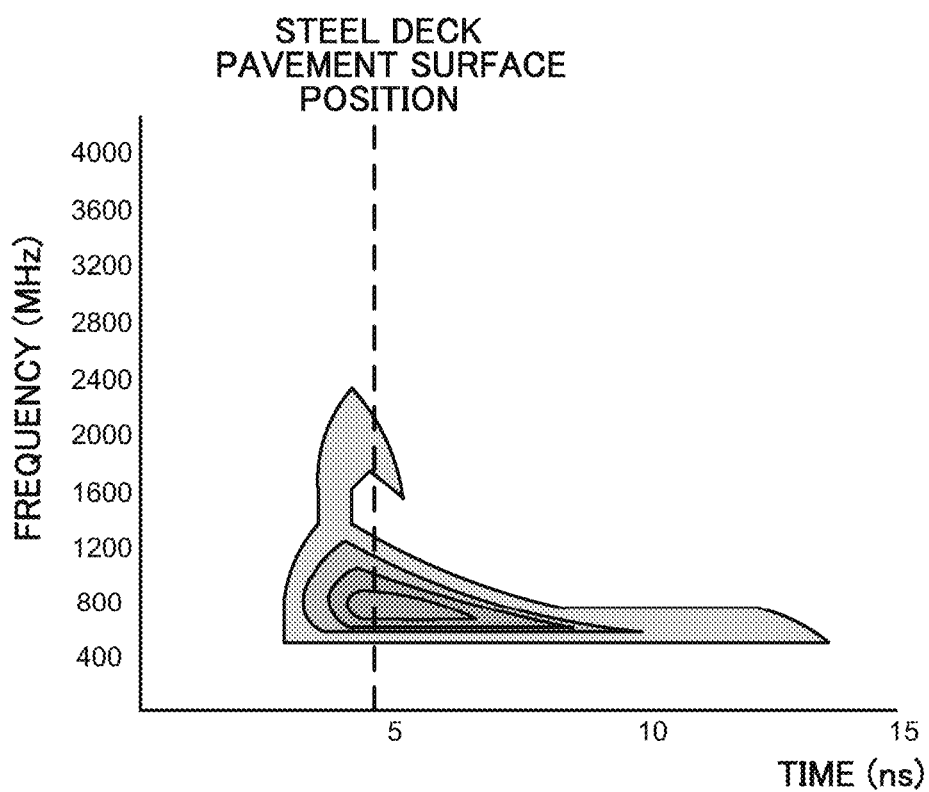
FIG. 8 is a time-frequency chart illustrating the reflected response in FIG. 7 as expressed after applying a Fourier transform.
Figure 9:
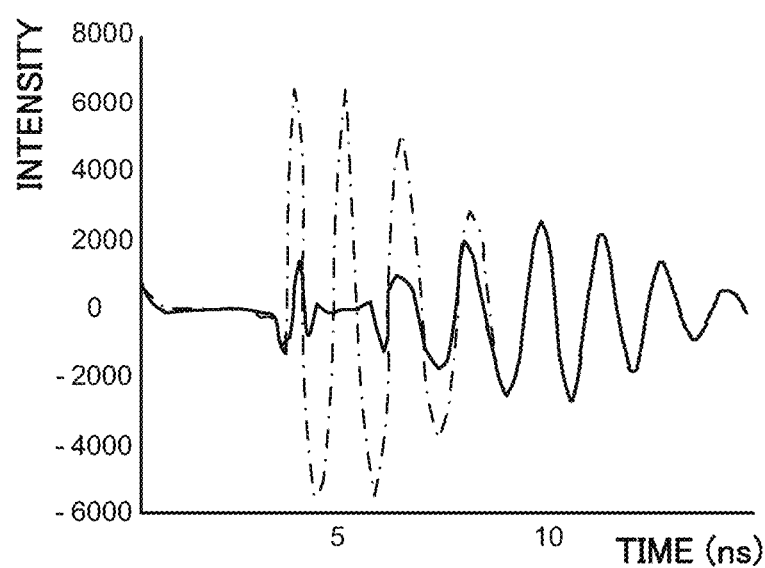
FIG. 9 is a diagram illustrating a reflected response from which a first frequency component has been removed.
Figure 10:
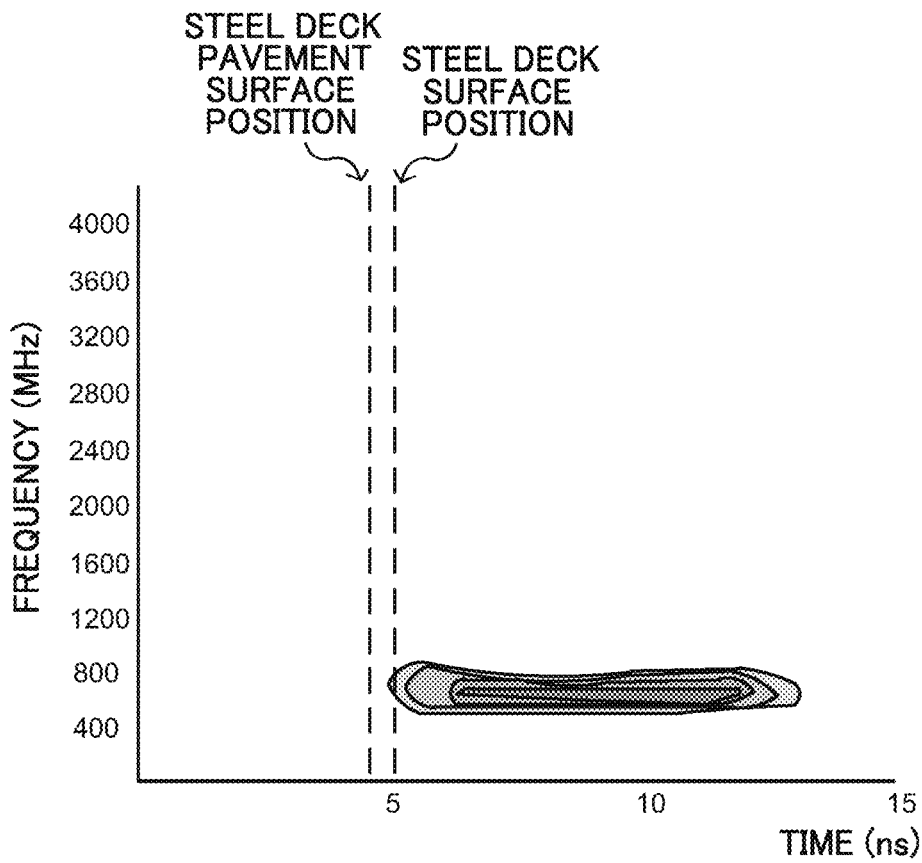
FIG. 10 is a time-frequency chart illustrating the reflected response in FIG. 9 as expressed after applying a Fourier transform.
Figure 11:
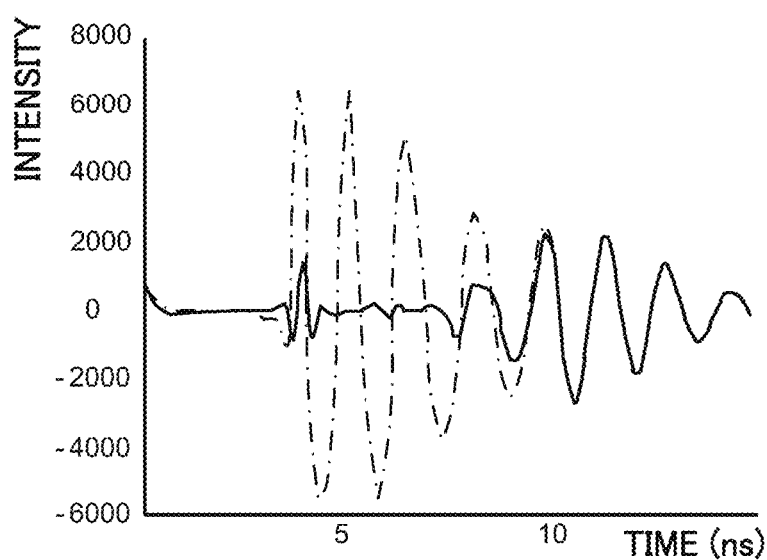
FIG. 11 is a diagram illustrating a reflected response from which a second frequency component has also been removed.
Figure 12:
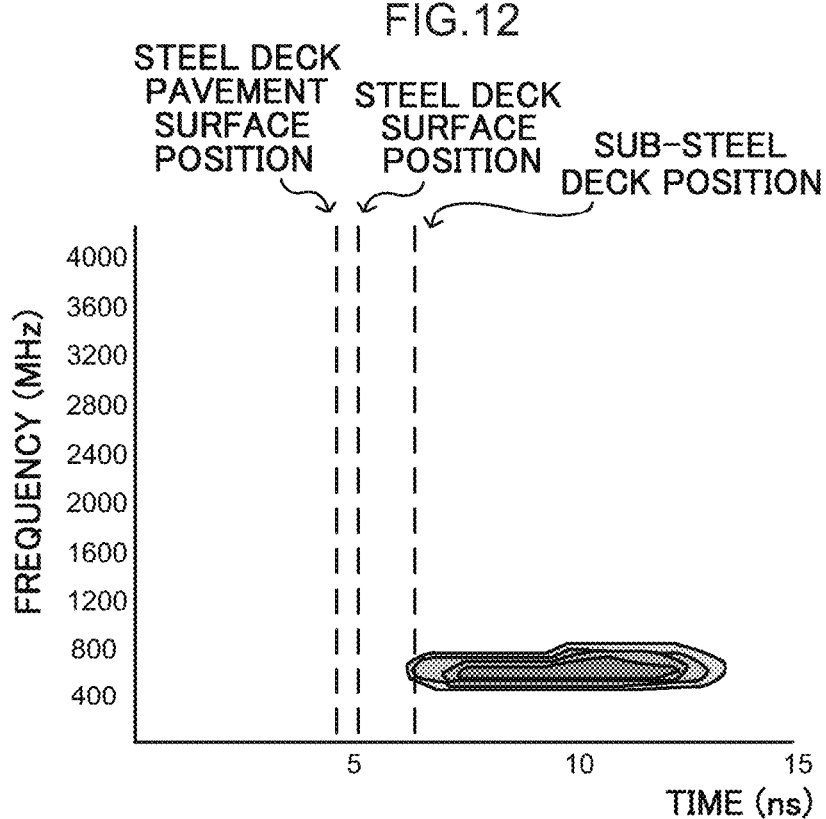
FIG. 12 is a time-frequency chart illustrating the reflected response in FIG. 11 as expressed after applying a Fourier transform.
Figure 13:
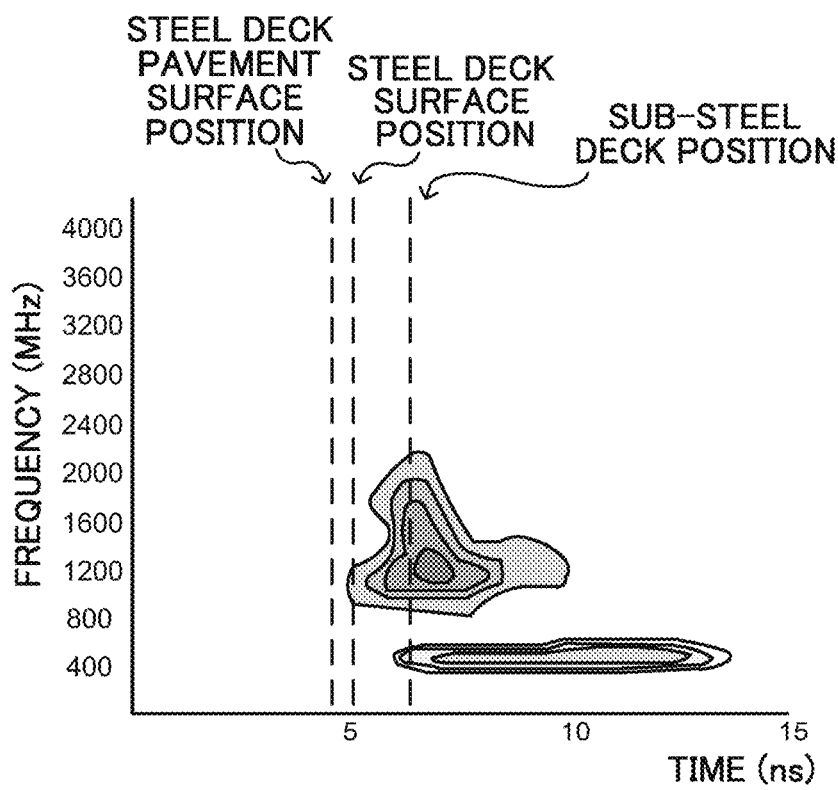
FIG. 13 is a time-frequency distribution chart obtained after removing a first frequency component and a second frequency component from a waveform obtained from a deck containing sound mastic asphalt.

FIG. 7 is a diagram illustrating a reflected response based on reflected response data acquired from the electromagnetic wave device. FIG. 8 is a time-frequency chart illustrating the reflected response in FIG. 7 as expressed after applying a Fourier transform. FIG. 9 is a diagram illustrating a reflected response from which the first frequency component has been removed. FIG. 10 is a time-frequency chart representing illustrating the reflected response in FIG. 9 as expressed after applying a Fourier transform. FIG. 11 is a diagram illustrating a reflected response from which the second frequency component has been removed. FIG. 12 is a time-frequency chart illustrating the reflected response in FIG. 11 as expressed after applying a Fourier transform. Note that FIG. 12 is a diagram explaining respective components of the reflected response. FIG. 13 is a time-frequency distribution chart obtained by removing the first frequency component and the second frequency component from a waveform obtained from a steel deck bridge containing sound mastic asphalt.

Note that in FIG. 7, FIG. 9, and FIG. 11, the horizontal axis represents time, and the vertical axis represents the signal intensity of the electromagnetic waves received. In FIG. 8, FIG. 10, and FIG. 12, the horizontal axis represents time, and the vertical axis represents frequency. In FIG. 8, FIG. 10, and FIG. 12, the signal intensity is represented by the shading density. The time represented by the horizontal axis in FIG. 7 to FIG. 12 is the time taken for the electromagnetic waves reflected by the steel deck bridge to be received. Since electromagnetic waves reflected from deeper locations of the steel deck bridge are received later by the electromagnetic wave device 20, the horizontal axis in FIG. 7 to FIG. 12 may be said to represent vertical direction depth positions of the steel deck bridge.

The reflected response waveform illustrated in FIG. 7 is obtained based on the reflected response data acquired from the electromagnetic wave device 20 by the acquisition section 100. The time-frequency distribution chart illustrated in FIG. 8 is obtained by applying a Fourier transform to the reflected response waveform illustrated in FIG. 7.

The time-frequency distribution chart illustrated in FIG. 8 includes the first frequency component expressing the surface-reflected response illustrated in FIG. 4 and the second frequency component expressing the steel deck-reflected response illustrated in FIG. 4. A frequency distribution accordingly appears at times corresponding to the position of the surface of the steel deck pavement, illustrated by the dotted line in FIG. 8.

The removal section 101 described previously removes the first frequency component from the waveform illustrated in FIG. 7 to give a waveform such as that illustrated in FIG. 9. In FIG. 9, the waveform prior to removing the first frequency component is illustrated by a single-dotted dashed line. The time-frequency distribution chart illustrated in FIG. 10 is obtained by performing a Fourier transform on the waveform illustrated in FIG. 9. The time-frequency distribution chart illustrated in FIG. 10 does not include the first frequency component expressing the surface-reflected response illustrated in FIG. 4, but does include the second frequency component expressing the steel deck-reflected response illustrated in FIG. 4. Thus, unlike in FIG. 8, a frequency distribution does not appear for times corresponding to positions (depths) within the steel deck pavement, as indicated by the dotted lines in FIG. 10.

The removal section 101 further removes the second frequency component from the waveform illustrated in FIG. 9 to give a waveform such as that illustrated in FIG. 11. In FIG. 11, the waveform prior to removing the first frequency component and the second frequency component is illustrated by a single-dotted dashed line. The time-frequency distribution chart illustrated in FIG. 12 is obtained by performing a Fourier transform on the waveform illustrated in FIG. 11. The time-frequency distribution chart illustrated in FIG. 12 includes neither the first frequency component expressing the surface-reflected response illustrated in FIG. 4, nor the second frequency component expressing the steel deck-reflected response illustrated in FIG. 4. Thus, unlike in FIG. 10, a frequency distribution does not appear for times corresponding to positions (depths) in the vicinity of the surface of the steel deck 98, as indicated by a dotted line in FIG. 12. On the other hand, a frequency distribution still appears for time-positions at a greater depth than the position (depth) of the steel deck (referred to as sub-steel deck positions).

Note that FIG. 12 is an example of a time-frequency distribution chart obtained by removing the first frequency component and the second frequency component from a waveform obtained when irradiating a steel deck bridge containing deteriorated mastic asphalt with electromagnetic waves.

FIG. 13 is an example of a time-frequency distribution chart obtained by removing the first frequency component and the second frequency component from a waveform obtained when irradiating a steel deck bridge containing sound (non-deteriorated) mastic asphalt with electromagnetic waves.

As illustrated in FIG. 13, when the first frequency component and the second frequency component have been removed from a waveform obtained from a steel deck bridge containing sound mastic asphalt, a frequency distribution appears at time-positions at a greater depth than the position (depth) of the steel deck (the sub-steel deck positions). Unlike in FIG. 12, a frequency distribution also appears in a frequency band corresponding to 1 GHz and above on the vertical axis.

The first frequency component and the second frequency component have a high electromagnetic wave reflection intensity, and therefore have a large effect on the display of frequency distribution in the time-frequency distribution chart. Thus, removing the first frequency component and the second frequency component enables the weak frequency components at time-positions at a greater depth than the steel deck to be made more visible.

Since the steel deck is made of metal, it would normally be expected that electromagnetic waves would be totally reflected by the steel deck, and that reflected electromagnetic waves would not be received from objects at a greater depth than the steel deck. However, as a result of multiple reflection of waves between the steel deck and the receiver elements of the electromagnetic wave device 20, it is possible to receive electromagnetic waves at a later time than the time at which reflected waves from the steel deck are received. Such electromagnetic waves are electromagnetic waves received at time-positions corresponding to a greater depth than the steel deck. Since these electromagnetic waves have passed through the inside of the mastic asphalt layer 97 plural times due to the multiple reflection, the mastic asphalt layer has a large effect on electromagnetic wave propagation. In cases in which damage to or deterioration is present in the mastic asphalt layer 97, the electromagnetic waves are scattered or absorbed due to cracks, warping, and the like within the mastic asphalt layer 97, attenuating the electromagnetic waves as they undergo multiple reflection. This is thought to be why the frequency distribution peak appearing in the frequency band of 1 GHz and above is diminished in such cases. Moreover, water ingress into the mastic asphalt layer 97 sometimes occurs as a result of deterioration. It is surmised that the electromagnetic waves are attenuated by the presence of such water, thereby diminishing the frequency distribution peak appearing in the frequency band of 1 GHz and above.

Conversely, if the mastic asphalt has not deteriorated, there is less dispersion of electromagnetic waves inside the mastic asphalt layer 97, and there is less of an effect on electromagnetic waves undergoing multiple reflection. The frequency distribution peak appearing in the frequency band of 1 GHz and above is thought to be more pronounced as a result.

Note that frequency components of less than 1 GHz may also appear in electromagnetic waves that have undergone multiple reflection. However, changes in frequency caused by damage to or deterioration of the mastic asphalt layer 97 and the surface of the steel deck 98 are less pronounced in frequency components of less than 1 GHZ, and more pronounced in frequency components of 1 GHz and above. It is therefore thought that trends in the frequency components of electromagnetic waves that have undergone multiple reflection will be more apparent in the distribution at 1 GHz and above. Thus, it has been found deterioration of the mastic asphalt can be determined by referring to the frequency distribution at 1 GHz and above. It is also known that corrosion due to water ingress develops at the surface (metal surface) of the steel deck 98 as a result of a drop in water resistance at locations where damage to or deterioration is present in the mastic asphalt. Thus, if locations of damage to or deterioration can be identified when evaluating damage to or deterioration of the mastic asphalt, locations of damage to or deterioration on the surface of the steel deck 98 can also be identified.

Note that although the present exemplary embodiment adopts 1 GHz as a reference value to discriminate between 1 GHz and above and less than 1 GHZ, the present disclosure is not limited to a reference value of 1 GHz. A specific frequency other than 1 GHZ may be employed as a reference value. This specific frequency may be set as appropriate, on the condition that a frequency distribution appears for electromagnetic waves that have undergone multiple reflection, and that a recognizable peak is present in the frequency distribution.

Moreover, electromagnetic waves that have undergone multiple reflection as described above may also be affected by the surface of the steel deck 98 if damage to or deterioration is present due to corrosion or the like. In cases in which this has an effect on the frequency distribution appearing in the frequency band of 1 GHZ and above, evaluation of damage to or deterioration of the surface of the steel deck 98 may be possible in addition to evaluation of damage to or deterioration of the mastic asphalt. However, the following explanation does not take the effects of damage to or deterioration of the surface of the steel deck 98 into consideration, and assumes that only damage to or deterioration of the mastic asphalt will have an effect on the frequency distribution appearing in the frequency band of 1 GHz and above.

Figure 14:
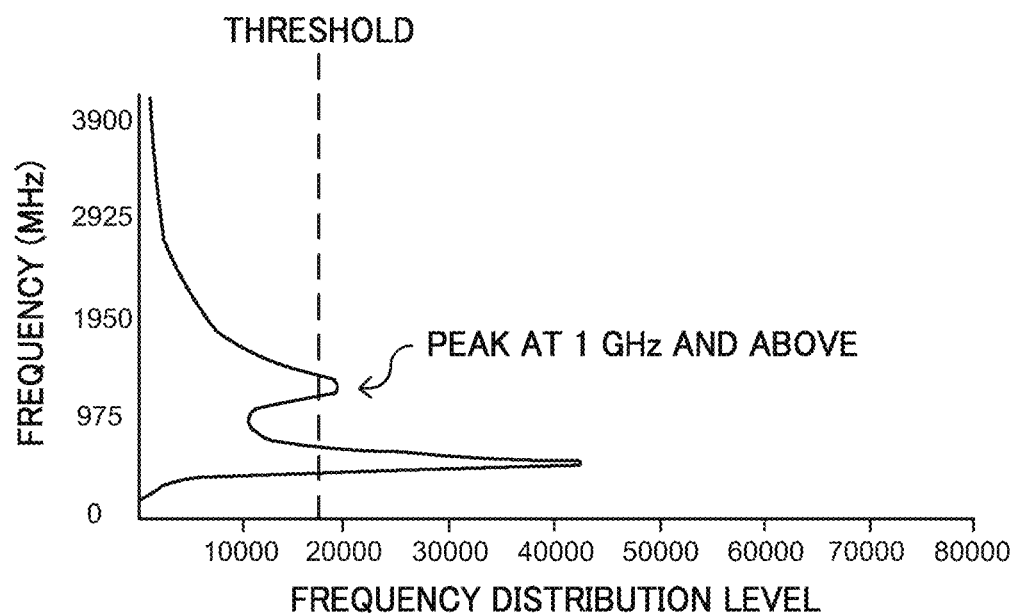
FIG. 14 is a diagram illustrating an example of a frequency distribution extracted from a waveform obtained from a deck containing sound mastic asphalt.
Figure 15:
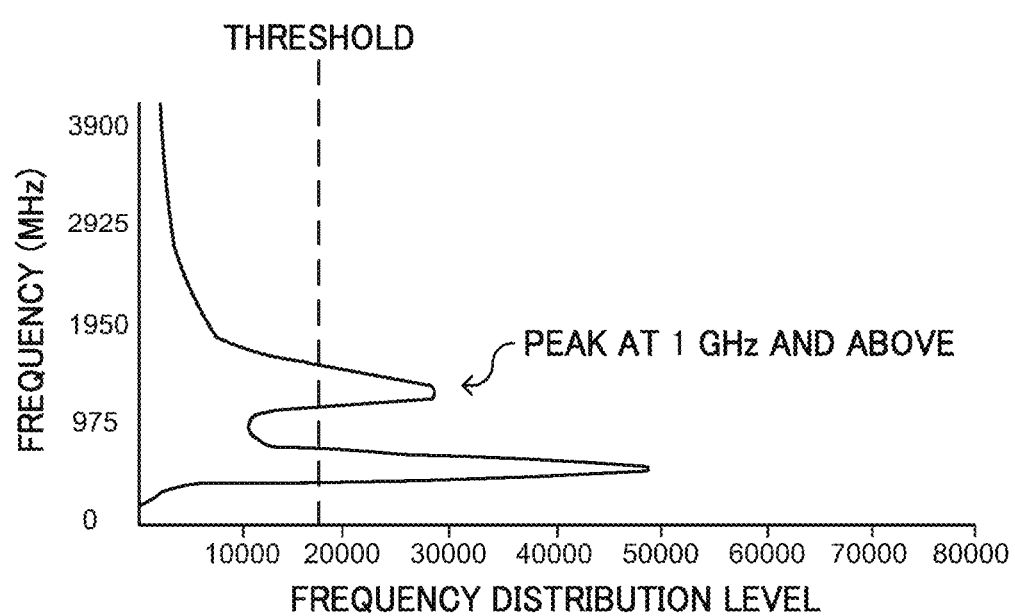
FIG. 15 is a diagram illustrating an example of a frequency distribution extracted from a waveform obtained from a deck containing sound mastic asphalt.
Figure 16:
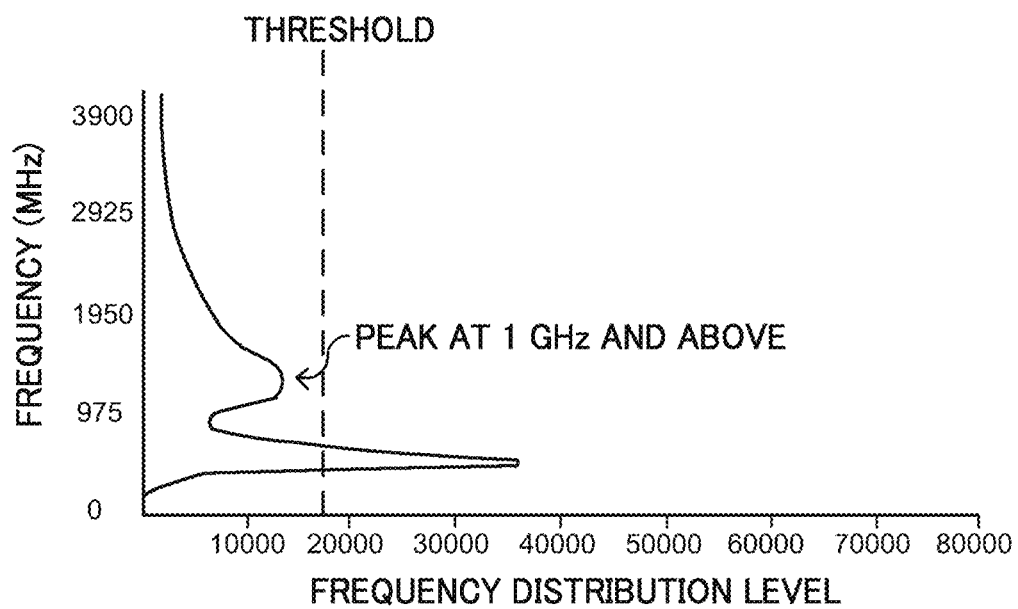
FIG. 16 is a diagram illustrating an example of a frequency distribution extracted from a waveform obtained from a deck containing deteriorated mastic asphalt.

FIG. 14 and FIG. 15 are diagrams illustrating examples of frequency distributions extracted from waveforms obtained from steel deck bridges containing sound mastic asphalt. FIG. 16 is a diagram illustrating an example of a frequency distribution extracted from a waveform obtained from a steel deck bridge containing deteriorated mastic asphalt.

As illustrated in FIG. 14 and FIG. 15, in the frequency distributions extracted from the waveforms obtained from steel deck bridges containing sound mastic asphalt, a peak in the frequency band of 1 GHz and above exhibits a high frequency distribution level. On the other hand, as illustrated in FIG. 16, in the frequency distribution extracted from the waveform obtained from the steel deck bridge containing deteriorated mastic asphalt, the peak in the frequency band of 1 GHz and above exhibits a low frequency distribution level. For example, if a frequency distribution level illustrated by dotted lines in FIG. 14 to FIG. 16 is set as a threshold, determination can be made that the steel deck bridge contains sound mastic asphalt in cases in which the peak is the threshold or greater, and that the steel deck bridge contains deteriorated mastic asphalt in cases in which the peak is below the threshold.

The threshold may for example be set in the following manner. Namely, the first frequency component and the second frequency component are removed from reflected responses obtained by irradiating plural samples of steel deck bridges containing sound mastic asphalt that has not deteriorated with electromagnetic waves. By performing this removal operation, reference frequency distributions corresponding to reflected response frequency distributions such as those illustrated in FIG. 14 and FIG. 15 are obtained. From these reference frequency distributions, an average of the frequency distribution levels of the peaks appearing in the frequency band of 1 GHz and above is then computed as a reference value. For example, a value such as 60%, 50%, or 40% of this reference value may be then set as the threshold. The threshold may be set as appropriate by a practitioner skilled in the art according to a permissible extent of deterioration of the mastic asphalt, and so on. For example, if a value of 40% of the reference value is set as the threshold, a steel deck bridge may be determined to have deteriorated when deterioration has reached 60% or greater.

Next, explanation follows regarding operation of the evaluation device 10.

Figure 17:
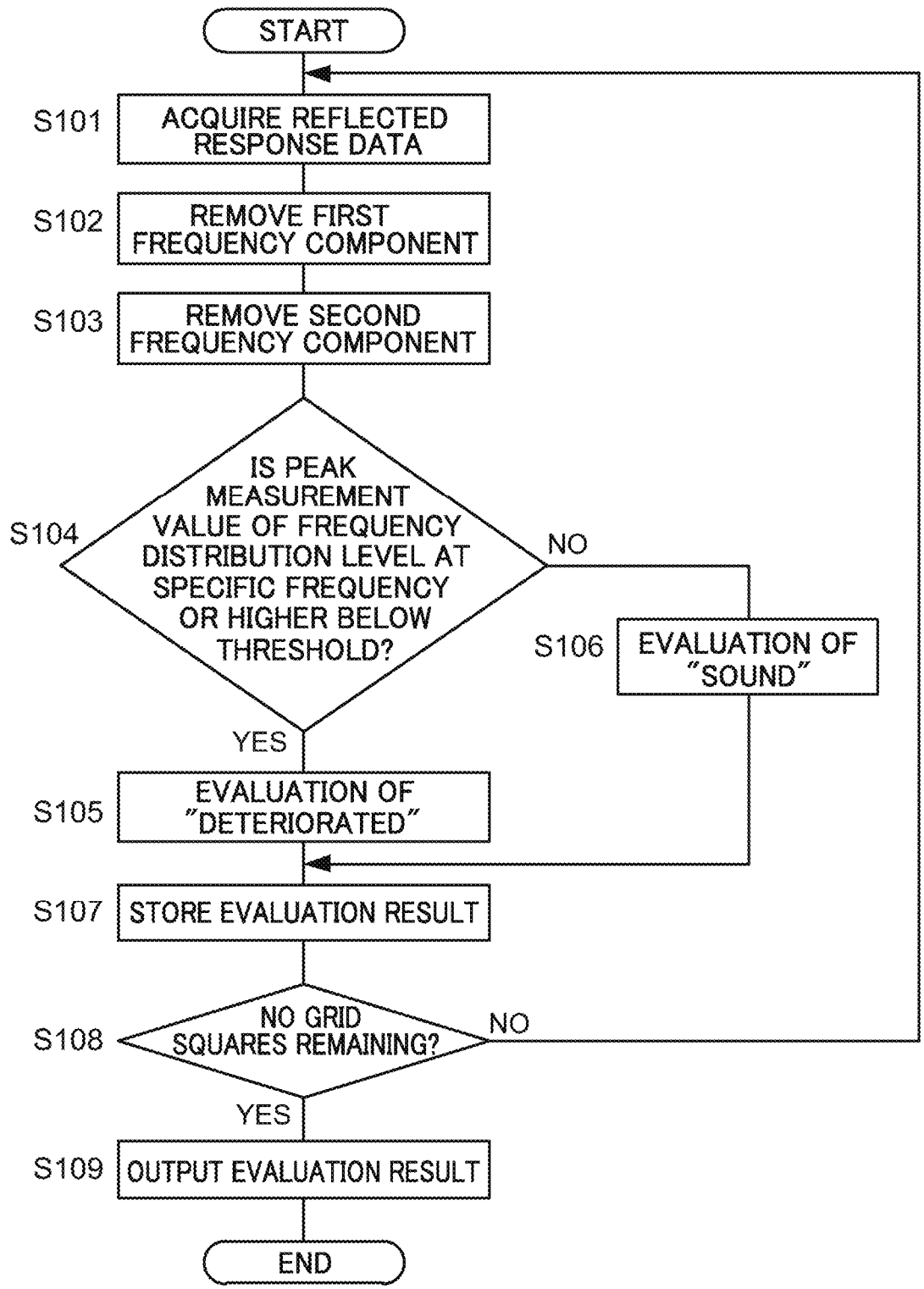
FIG. 17 is a flowchart illustrating a flow of a steel deck bridge evaluation program executed by an evaluation device.

FIG. 17 is a flowchart illustrating a flow of the steel deck bridge evaluation program executed by the evaluation device. The steel deck bridge evaluation program is executed by the CPU 11 reading the steel deck bridge evaluation program from the ROM 12 or the storage 14 and expanding and executing the program in the RAM 13.

The CPU 11 acts as the acquisition section 100 to acquire reflected response data relating to the electromagnetic wave reflected response from the electromagnetic wave device 20 (step S101).

The CPU 11 removes the first frequency component (step S102) and also removes the second frequency component (step S103) from the acquired reflected response data.

The CPU 11 determines whether or not a peak value (peak measurement value) of the frequency distribution level of the frequency distribution at a specific frequency (for example 1 GHZ) or higher is below a threshold (step S104). In cases in which the peak value is below the threshold (step S104: YES) as illustrated in FIG. 16, the CPU 11 makes an evaluation of "deteriorated" for the mastic asphalt of the steel deck bridge (step S105), and processing proceeds to step S107.

On the other hand, in cases in which the peak value is the threshold or greater (step S104: NO) as illustrated in FIG. 14, the CPU 11 makes an evaluation of "sound" for the mastic asphalt of the steel deck bridge (step S106), and processing proceeds to step S107.

The CPU 11 then stores the evaluation result in the storage 14 (step S107). The CPU 11 then determines whether or not any more grid squares remain to be processed (step S108). In cases in which there are no remaining grid squares to be processed (step S108: YES), the CPU 11 reads the evaluation results from the storage 14 and outputs these results to the display section 16 and the like (step S109). In cases in which there is a grid square remains (step S108: NO), the CPU 11 repeats the processing from step S101.

As described above, in the evaluation device 10 of the present exemplary embodiment, the first frequency component and the second frequency component are removed from the reflected response obtained from the steel deck bridge in order to extract frequency components of electromagnetic waves that have undergone multiple reflection in the mastic asphalt layer 97. The degree of damage to or deterioration of the mastic asphalt contained in the steel deck bridge can then be evaluated by comparing the peak value at the specific frequency or higher of the extracted frequency components against the threshold. This evaluation enables locations of damage to or deterioration of the mastic asphalt to be identified. Furthermore, since corrosion due to water ingress develops at the surface (metal surface) of the steel deck 98 as a result of a drop in water resistance at locations of damage to or deterioration in the mastic asphalt, locations of damage to or deterioration on the surface of the steel deck 98 can also be identified.

In particular, in the above exemplary embodiment, the threshold value is set to a predetermined proportion of a reference value obtained from samples containing sound mastic asphalt, and a steel deck bridge is evaluated as having deteriorated in cases in which the peak measurement value is below the threshold. This enables simple determination as to whether or not a steel deck bridge has deteriorated to be performed using a threshold that corresponds to a proportion of a specific state of deterioration.

Moreover, in the above exemplary embodiment, damage to or deterioration of a steel deck bridge is evaluated for plural positions on the surface of the steel deck bridge based on grid squares. This enables the evaluation device 10 to identify regions of a planar face of the steel deck bridge that have deteriorated and regions that have not deteriorated in the form of surface areas or ranges.

Note that in the flowchart described above, the first frequency component is removed at step S102, and the second frequency component is removed at step S103. However, in the present exemplary embodiment, the first frequency component may be removed after the second frequency component has been removed, or the first frequency component and the second frequency component may be removed at the same time.

MODIFIED EXAMPLE

In the above exemplary embodiment, the mastic asphalt is determined to have deteriorated in cases in which the peak value of the frequency distribution level at the specific frequency or higher is below the threshold. However, the present disclosure is not limited to determining whether or not deterioration has occurred based on a comparison with a threshold. As a modified example, a proportional difference between the above-described reference value obtained by measuring steel deck bridges that have not deteriorated and the above-described peak measurement value obtained by measuring a steel deck bridge configuring a measurement target may be used to evaluate deterioration in terms of proportion.

Explanation follows regarding operation of the evaluation device 10 in such a case.

Figure 18:
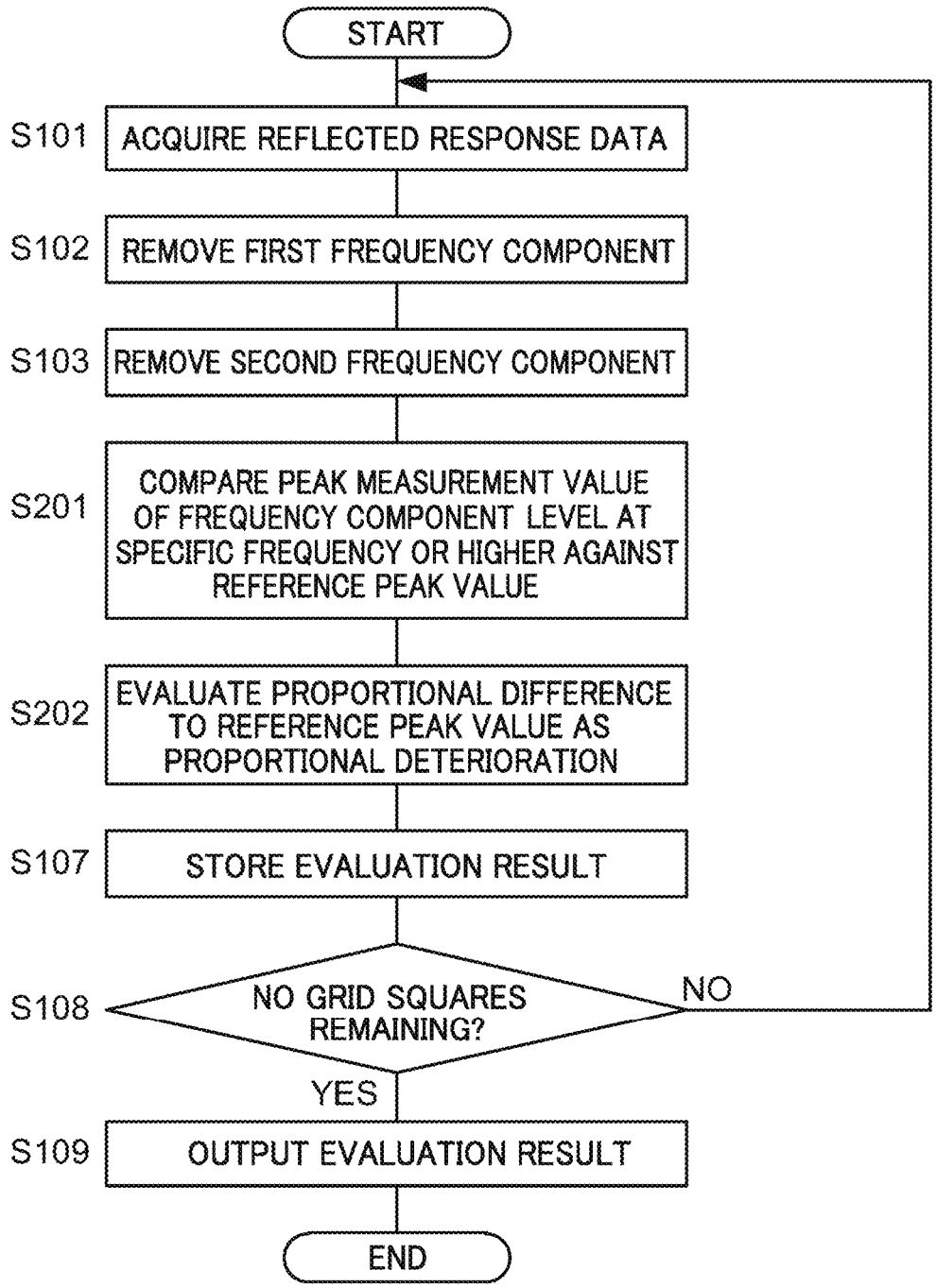
FIG. 18 is a flowchart illustrating a modified example of a flow of a steel deck bridge evaluation program executed by an evaluation device.

FIG. 18 is a flowchart illustrating a flow of a steel deck bridge evaluation program executed by an evaluation device according to the modified example.

Note that steps S101 to S103 and S107 to S109 illustrated in FIG. 18 are the same as those in FIG. 17.

The CPU 11 acquires the reflected response data acquired by irradiating the steel deck bridge configuring the measurement target with electromagnetic waves (step S101), and removes the first frequency component and the second frequency component (steps S102 and S103).

The CPU 11 then compares a peak measurement value of the frequency component level at the specific frequency or higher in the frequency distribution from which the first frequency component and the second frequency component have been removed against a reference peak value (step S201).

The CPU 11 then evaluates a proportional difference between the reference peak value and the peak measurement value as proportional deterioration (step S202). For example, in cases in which the peak measurement value is 40% as a proportion of the reference peak value, the proportional difference between the reference peak value and the peak measurement value is 60%. In such a case, the CPU 11 evaluates the degree of deterioration to be 60%.

As described above, the modified example enables the degree of deterioration to be evaluated quantitatively, instead of by performing a binary determination of either "deteriorated" or "sound" as in the exemplary embodiment described previously.

The above processing may be implemented by a dedicated hardware circuit. In such cases, the processing may be executed by a single piece of hardware, or plural pieces of hardware.

Alternatively, a program for operation of the steel deck bridge evaluation device 10 may be provided by a non-transitory recording medium such as universal serial bus (USB) memory, a flexible disc, or compact disc read only memory (CD-ROM), or may be provided online over a network such as the internet. In such cases, the program recorded in a computer-readable recording medium is normally transmitted to and stored in memory, storage, or the like. Alternatively the program may be provided as stand-alone application software, and one function of the steel deck bridge evaluation device 10 may be to implement software of respective devices.

Supplement 1

A steel deck bridge evaluation device for evaluating damage to or deterioration of a steel deck bridge in which a steel deck is embedded under asphalt, the evaluation device including
- at least one processor, the processor being configured to:
- acquire reflected response data relating to a reflected response to an electromagnetic wave irradiated through a surface of the steel deck bridge in a depth direction of the steel deck bridge;
- remove a first frequency component obtained by reflection of the electromagnetic wave at the surface of the steel deck bridge and a second frequency component obtained by reflection of the electromagnetic wave at the steel deck from a reflected response frequency distribution of the reflected response expressing the acquired reflected response data; and
- evaluate damage to or deterioration of the steel deck bridge using a peak measurement value that is a peak value of a frequency component level corresponding to a specific frequency or higher, in the reflected response frequency distribution from which the first frequency component and the second frequency component have been removed.

Supplement 2

A non-transitory storage medium stored with a program capable of being executed by a computer in order to execute steel deck bridge evaluation processing to evaluate damage to or deterioration of a steel deck bridge in which a steel deck is embedded under asphalt,
- the steel deck bridge evaluation processing including:
- acquiring reflected response data relating to a reflected response to an electromagnetic wave irradiated through a surface of the steel deck bridge in a depth direction of the steel deck bridge;
- removing a first frequency component obtained by reflection of the electromagnetic wave at the surface of the steel deck bridge and a second frequency component obtained by reflection of the electromagnetic wave at the steel deck from a reflected response frequency distribution of the reflected response expressing the acquired reflected response data; and
- evaluating damage to or deterioration of the steel deck bridge using a peak measurement value that is a peak value of a frequency component level corresponding to a specific frequency or higher, in the reflected response frequency distribution from which the first frequency component and the second frequency component have been removed.

The invention claimed is:

1. A steel deck bridge evaluation device for evaluating damage to or deterioration of a steel deck bridge in which a steel deck is embedded under asphalt, the evaluation device comprising:
at least one processor, the processor being configured to:
acquire reflected response data relating to a reflected response to an electromagnetic wave irradiated through a surface of the steel deck bridge in a depth direction of the steel deck bridge;
remove a first frequency component obtained by reflection of the electromagnetic wave at the surface of the steel deck bridge and a second frequency component obtained by reflection of the electromagnetic wave at the steel deck from a reflected response frequency distribution of the reflected response expressing the reflected response data; and
evaluate damage to or deterioration of the steel deck bridge using a peak measurement value that is a peak value of a frequency component level corresponding to a specific frequency or higher, in the reflected response frequency distribution from which the first frequency component and the second frequency component have been removed.

2. The steel deck bridge evaluation device of claim 1, wherein the processor is configured to:
take, as a reference value, a peak value of a frequency component level corresponding to the specific frequency or higher, in a reference frequency distribution that is a reflected response frequency distribution obtained by removing the first frequency component and the second frequency component from a reflected response acquired by irradiating an electromagnetic wave into a steel deck bridge that has not deteriorated; and
evaluate a degree of damage to or deterioration of the steel deck bridge by comparing the peak measurement value with the reference value.

3. The steel deck bridge evaluation device of claim 2, wherein the processor is configured to evaluate damage to or deterioration of the steel deck bridge at a plurality of positions on the surface of the steel deck bridge.

4. The steel deck bridge evaluation device of claim 2, wherein the processor is configured to perform evaluation by taking, as a proportional deterioration, a proportion of a difference between the reference value and the peak measurement value relative to the reference value.

5. The steel deck bridge evaluation device of claim 4, wherein the processor is configured to evaluate damage to or deterioration of the steel deck bridge at a plurality of positions on the surface of the steel deck bridge.

6. The steel deck bridge evaluation device of claim 2, wherein the processor is configured to:
set a predetermined proportion relative to the reference value as a threshold; and
evaluate the steel deck bridge as having deteriorated in a case in which the peak measurement value is lower than the threshold.

7. The steel deck bridge evaluation device of claim 6, wherein the processor is configured to evaluate damage to or deterioration of the steel deck bridge at a plurality of positions on the surface of the steel deck bridge.

8. The steel deck bridge evaluation device of claim 1, wherein the processor is configured to evaluate damage to or deterioration of the steel deck bridge at a plurality of positions on the surface of the steel deck bridge.

9. A steel deck bridge evaluation method for evaluating damage to or deterioration of a steel deck bridge in which a steel deck is embedded under asphalt, the evaluation method comprising:
acquiring reflected response data relating to a reflected response to an electromagnetic wave irradiated through a surface of the steel deck bridge in a depth direction of the steel deck bridge;
removing a first frequency component obtained by reflection of the electromagnetic wave at the surface of the steel deck bridge and a second frequency component obtained by reflection of the electromagnetic wave at the steel deck from a reflected response frequency distribution of the reflected response expressing the acquired reflected response data; and
evaluating damage to or deterioration of the steel deck bridge using a peak measurement value that is a peak value of a frequency component level corresponding to a specific frequency or higher, in the reflected response frequency distribution from which the first frequency component and the second frequency component have been removed.

10. A non-transitory storage medium stored with a program capable of being executed by a computer in order to execute steel deck bridge evaluation processing to evaluate damage to or deterioration of a steel deck bridge in which a steel deck is embedded under asphalt, the steel deck bridge evaluation processing comprising:

acquiring reflected response data relating to a reflected response to an electromagnetic wave irradiated through a surface of the steel deck bridge in a depth direction of the steel deck bridge;

removing a first frequency component obtained by reflection of the electromagnetic wave at the surface of the steel deck bridge, and a second frequency component obtained by reflection of the electromagnetic wave at the steel deck from a reflected response frequency distribution of the reflected response expressing the acquired reflected response data; and evaluating damage to or deterioration of the steel deck bridge using a peak measurement value that is a peak value of a frequency component level corresponding to a specific frequency or higher, in the reflected response frequency distribution from which the first frequency component and the second frequency component have been removed.

* * * * *